US012642931B2

(12) United States Patent (10) Patent No.: US 12,642,931 B2
Luo et al. (45) Date of Patent: Jun. 2, 2026

(54) GAS INHALATION DEVICE WITH CONSTANT CONCENTRATION OF GAS ENTERING RESPIRATORY TRACT AND WITHOUT RESPIRATORY RESISTANCE

(71) Applicant: Yuanming Luo, Guangzhou (CN)

(72) Inventors: Yuanming Luo, Guangzhou (CN);
Yingmei Luo, Guangzhou (CN);
Nanshan Zhong, Guangzhou (CN)

(73) Assignee: Yuanming Luo, Guangzhou (CN)

( * ) Notice: Subject to any disclaimer, the term of this patent is extended or adjusted under 35 U.S.C. 154(b) by 733 days.

(21) Appl. No.: 17/418,932

(22) PCT Filed: Dec. 12, 2019

(86) PCT No.: PCT/CN2019/124746
§ 371 (c)(1),
(2) Date: Jun. 28, 2021

(87) PCT Pub. No.: WO2020/135062
PCT Pub. Date: Jul. 2, 2020

(65) Prior Publication Data
US 2022/0062576 A1 Mar. 3, 2022

(30) Foreign Application Priority Data

Dec. 29, 2018 (CN) .......................... 201811629308.7

(51) Int. Cl.
*A61M 16/06* (2006.01)
*A61M 16/08* (2006.01)
(Continued)

(52) U.S. Cl.
CPC .... *A61M 16/0611* (2014.02); *A61M 16/0633* (2014.02); *A61M 16/0875* (2013.01);
(Continued)

(58) Field of Classification Search
CPC ...... A61M 16/00–026; A61M 16/0611; A61M 16/0633; A61M 16/0875; A61M 16/1005;
(Continued)

(56) References Cited

U.S. PATENT DOCUMENTS 2,007,440 A * 7/1935 Brand .................. A62B 18/003
128/205.24
2,675,803 A * 4/1954 Kaslow ................. A61M 16/06
128/206.28
(Continued)

FOREIGN PATENT DOCUMENTS

CN 104815376 8/2015
CN 204709591 U * 10/2015
(Continued)

OTHER PUBLICATIONS

CN 108245756 A description translation accessed Mar. 7, 2024 (Year: 2024).*
(Continued)

*Primary Examiner* — Bradley H Philips
*Assistant Examiner* — Kira B Daher
(74) *Attorney, Agent, or Firm* — Michael Fedrick; LOZA & LOZA, LLP

(57) ABSTRACT

The present invention provides a gas inhalation device with a constant concentration of gas entering the respiratory tract and without respiratory resistance, including: a mask, a gas source and a gas mixer, wherein the mask is a container that is capable of holding 50-1000 ml of gas, a proximal end of the mask is a soft cushion for fitting the face and surrounded by a catheter, the catheter is provided with a plurality of small orifices communicating with an inner cavity of the mask, one end of the catheter is connected to one end of an adapter tube, the other end of the adapter tube is connected to a gas delivery pipe, the gas delivery pipe is a catheter (Continued)

connecting the adapter tube and the gas source or the gas mixer; a distal end of the mask is provided with a huge orifice or a plurality of large orifices to ensure unobstructed gas in and out, with almost no airflow resistance, and an internal pressure of the mask cavity is always zero; one or two headband interfaces are provided on both sides of the mask's outer layer for connecting a headband fixing the mask to ensure that the mask is stably fixed on the face.

16 Claims, 9 Drawing Sheets

(51) Int. Cl.
    *A61M 16/10*     (2006.01)
    *A61M 16/12*     (2006.01)

(52) U.S. Cl.
    CPC ........ *A61M 16/1005* (2014.02); *A61M 16/12* (2013.01); *A61M 2202/02* (2013.01); *A61M 2202/0208* (2013.01); *A61M 2202/0225* (2013.01); *A61M 2202/025* (2013.01)

(58) Field of Classification Search
    CPC ...... A61M 16/12–127; A61M 16/0683; A61M 16/06; A61M 16/104; A61M 2202/02; A61M 2202/0208; A61M 2202/0225; A61M 2202/025; A61M 2205/33; A62B 18/003
    See application file for complete search history.

(56)           References Cited

U.S. PATENT DOCUMENTS

| | | | | |
|---|---|---|---|---|
| 3,067,741 A * | 12/1962 | Croasdaile | ........... | A62B 18/025 |
| | | | | 128/205.17 |
| 3,977,432 A * | 8/1976 | Vidal | .................. | A61M 16/127 |
| | | | | 137/893 |
| 4,201,205 A * | 5/1980 | Bartholomew | ....... | A61M 16/06 |
| | | | | 128/205.25 |
| 4,231,363 A * | 11/1980 | Grimes | ................. | A61M 16/06 |
| | | | | 128/206.28 |
| 4,354,488 A * | 10/1982 | Bartos | ................... | A61M 16/06 |
| | | | | 128/205.25 |
| 4,702,240 A * | 10/1987 | Chaoui | ................. | A61M 16/12 |
| | | | | 128/205.24 |
| 5,005,571 A * | 4/1991 | Dietz | ................... | A61M 16/06 |
| | | | | 128/207.18 |
| 5,615,669 A * | 4/1997 | Olsson | .................. | A61M 16/12 |
| | | | | 128/203.14 |
| 8,733,356 B1 * | 5/2014 | Roth | ................... | A62B 18/003 |
| | | | | 128/205.27 |
| 2003/0000532 A1 | 1/2003 | Bowman | | |
| 2006/0196510 A1 * | 9/2006 | McDonald | ........... | A61M 16/06 |
| | | | | 128/205.25 |
| 2012/0285448 A1 | 11/2012 | Dugan | | |
| 2014/0366890 A1 * | 12/2014 | Tao | ..................... | A61M 16/009 |
| | | | | 128/849 |
| 2015/0335847 A1 * | 11/2015 | Matsubara | ........ | A61M 16/0816 |
| | | | | 128/205.25 |
| 2016/0082220 A1 * | 3/2016 | Barker | .............. | A61M 16/1005 |
| | | | | 128/203.12 |
| 2016/0121071 A1 * | 5/2016 | Moon | ................. | A61M 16/142 |
| | | | | 128/200.14 |
| 2016/0263340 A1 * | 9/2016 | Fenwick | ............... | A61M 16/06 |
| 2018/0272099 A1 * | 9/2018 | Bottom | ............ | A61M 16/1005 |
| 2020/0139074 A1 * | 5/2020 | Longest, Jr. | .......... | A61M 16/16 |

FOREIGN PATENT DOCUMENTS

| | | | | |
|---|---|---|---|---|
| CN | 205198642 | 5/2016 | | |
| CN | 205287171 | 6/2016 | | |
| CN | 107405508 | 11/2017 | | |
| CN | 108245756 A * | 7/2018 | ........ | A61M 16/0605 |
| CN | 108568023 | 9/2018 | | |
| GB | 551609 A * | 3/1943 | ........... | A62B 18/025 |

OTHER PUBLICATIONS

Batool, Garg "Appropriate Use of Oxygen Delivery Devices" Jan. 12, 2017, The Open Anesthesiology Journal (Year: 2017).*
CN-204709591-U description (Year: 2015).*

* cited by examiner

GAS INHALATION DEVICE WITH CONSTANT CONCENTRATION OF GAS ENTERING RESPIRATORY TRACT AND WITHOUT RESPIRATORY RESISTANCE

CROSS-REFERENCE TO RELATED APPLICATIONS

This is the US National Stage of International Patent Application No. PCT/CN2019/124746 filed Dec. 12, 2019, which claims priority to Chinese Patent Application No. 201811629308.7 filed Dec. 29, 2018.

TECHNICAL FIELD

The present invention relates to a medical treatment device, and in particular to a gas inhalation device with a constant concentration of gas entering the respiratory tract and without respiratory resistance.

BACKGROUND

The implementation of gas therapy, such as oxygen therapy in respiratory failure, and $CO_2$ treatment of central sleep apnea, require a gas inhalation device, especially a gas inhalation device with a constant concentration of inhaled gas. $CO_2$ is a stimulant driven by the respiratory center, but too high $CO_2$ concentration can cause anesthesia in the respiratory center. It is very important to control the amount of $CO_2$ inhaled. The main cause of heart failure combined with central apnea is the decrease in the partial pressure of $CO_2$ in the blood. Inhalation of $CO_2$ can eliminate central sleep apnea in patients with heart failure. However, the concentration of $CO_2$ during central sleep apnea is slightly different from the blood $CO_2$ during normal breathing. When the concentration of the inhaled $CO_2$ is too low, it will not have a therapeutic effect, and if it is too high, it will cause arousal. An accurate control of the inhalation concentration of $CO_2$ can eliminate central sleep apnea without causing excessive arousal and improve sleep quality. The currently used $CO_2$ inhalation mask is an ordinary oxygen mask (patent No. ZL 2016 1 0251692.6). Its working principle is to use a high-pressure gas source (including a gas source above atmospheric pressure generated by a gas generator or a gas mixer) to be delivered to the patient through a nasal cannula or a mask. Because the mask is small and the storage capacity is small, when the patient's inhalation volume is greater than the delivery flow rate, the resistance must be overcome to obtain gas from outside the mask, causing additional inhalation resistance. When the patient exhales, it is discharged through small orifices on both sides of the mask. Since the apertures of the small orifices on both sides of the mask cannot be too large to prevent excessive air from entering the mask during inhalation to decrease the concentration of inhaled gas. If the apertures of the small orifices on both sides of the mask are small, it will affect the discharge of expiratory gas, causing air retention and discomfort. In order to discharge the expiratory gas completely, sometimes the headband has to be loosened to allow the air to escape from the gap between the mask and the face. Since patients with heart failure and central sleep apnea are often accompanied by insomnia, the additional breathing resistance will further aggravate the patient's discomfort and impair sleep quality of patients.

The maintenance of life depends on oxygen. A plurality of types of oxygen therapy devices are present in clinical practice, but they all have common shortcomings, including the inhaled gas being diluted by the surrounding gas, being difficult to perform high-flow oxygen inhalation, and being unable to accurately control the concentration of the inhaled oxygen. Clinically, a mask that can significantly increase the oxygen concentration is present. It has an oxygen storage bag and three one-way valves. A one-way valve and associated small vents are respectively provided on both sides of the mask body for the discharge of expiratory gas. The other one-way valve is provided between the mask and the oxygen storage bag for the patient to inhale the gas in the oxygen storage bag and prevent the expiratory gas from entering the oxygen storage bag. Since the opening of the valve requires a driving pressure, $CO_2$ retention in patients with respiratory muscle insufficiency may be aggravated. In addition, the vents associated with the valves on both sides of the mask are small, which makes it difficult to completely discharge the expiratory gas, part of the expiratory gas needs to overcome resistance to exit from the gap between the mask and the face, causing poor exhalation and aggravating $CO_2$ retention.

Recent studies have found that inhaling helium and hydrogen has certain clinical value for some diseases. The inhalation of these gases also requires a gas inhalation device, and the concentration of the gas entering the respiratory tract is required to be fixed and constant to ensure the safety of treatment. However, currently no gas inhalation device with a constant concentration of gas entering the respiratory tract and without expiratory gas retention and respiratory resistance exists.

SUMMARY OF THE INVENTION

In order to overcome the problems existing in the existing gas inhalation technology, an objective of the present invention is to provide a gas inhalation device with a constant concentration of gas entering the respiratory tract and without respiratory resistance. The gas inhalation device can make the concentration of the gas entering the respiratory tract constant without expiratory gas retention and respiratory resistance.

The object of the present invention is achieved through the following technical solutions. A gas inhalation device with a constant concentration of gas entering the respiratory tract and without respiratory resistance, including: a mask, a gas source and a gas mixer, wherein the mask is a container that is capable of holding 50-1000 ml of gas, a proximal end of the mask is a soft cushion for fitting the face and surrounded by a catheter, the catheter is provided with a plurality of small orifices communicating with an inner cavity of the mask, one end of the catheter is connected to one end of an adapter tube, the other end of the adapter tube is connected to a gas delivery pipe, the gas delivery pipe is a catheter connecting the adapter tube and the gas source or the gas mixer; a distal end of the mask is provided with a huge orifice or a plurality of large orifices to ensure unobstructed gas in and out, with almost no airflow resistance, and an internal pressure of the mask cavity is always zero; one or two headband interfaces are provided on both sides of the mask's outer layer for connecting a headband fixing the mask to ensure that the mask is stably fixed on the face; when a patient receiving gas treatment wears the mask and the mask is communicated with the gas source and the gas mixer, the gas from the mixer is continuously delivered into the cavity at the proximal end of the mask at a constant concentration and flow rate through the gas delivery pipe and the catheter, and discharged from the large orifices at the distal end of the mask, and because the gas from the mixer is continuously injected into the mask cavity and expels the expiratory gas from the large orifices at the distal end of the mask, forming a gas inhalation device with a constant concentration of gas entering the respiratory tract and without expiratory gas retention and respiratory resistance.

The mask is an open mask that is capable of holding up to 1000 ml of gas, and the distal end of the mask is provided with one or more large orifices.

The proximal end of the mask is provided with one or more inlets communicating with the mask cavity to receive the gas from the mixer; and the gas that enters the mask cavity from the proximal end of the mask is discharged from the large orifices at the distal end of the mask together with the expiratory gas.

The internal pressure of the mask is always zero, and the mask is lightly attached to the face to avoid leakage without necessarily applying pressure on the face.

After a patient wears the mask, the gas from the gas mixer enters the mask cavity from the proximal end of the mask for the patient to inhale or to be discharged from the large orifices at the distal end.

The gas delivered into the mask cavity are different medical gases, including oxygen, $CO_2$, hydrogen and helium, and the concentration of the gas delivered into the mask cavity is equal to that of the gas entering the respiratory tract.

The gas with a constant concentration and flow rate delivered into the mask is either from the gas mixer or directly from the gas source including a gas cylinder and a hospital central gas supply system.

The total area of the large orifices at the distal end of the mask is large, the gas flow resistance is negligible, and the mask is lightly attached to the face without necessarily applying pressure to seal.

If the gas flow from the gas mixer cannot meet the patient's inhalation needs, the mixer gas staying at the proximal end of the mask before inhaling is used as a supplement to keep the concentration of the gas entering the respiratory tract unchanged.

The concentration of various gases delivered into the mask cavity is selectable, for example, oxygen from 21% to 100% pure oxygen; and the concentration of $CO_2$ from 0%-10%.

Compared with the prior art, the present invention has the following advantages:

After the patient wears the mask and the adapter tube at the proximal end of the mask is connected to a gas mixer or gas source with a constant output flow rate (for example, 60 L/min) through the connector and the gas delivery pipe, the gas will be evenly delivered to enter the mask cavity around the proximal end of the mask and flows out from the distal end of the mask. Because a plurality of large orifices or one huge orifice are provided at the distal end of the mask with a large aperture and with almost no resistance and the pressure in the mask being always zero, all the gas in the mask is discharged through the large or huge orifices at the distal end of the mask. Even if the connection between the mask and the face is not completely tight, since the gas flow into and out of the large orifices or the huge orifice at the distal end is far less resistant than the connection between the mask and the face, all gas in the mask will still be discharged from the distal end of the mask. Because the gas source or the gas mixer is connected to the catheter surrounding the proximal end of the mask and with a plurality of small orifices through the gas delivery pipe and the adapter tube at a constant flow rate, and the small orifices on the catheter communicate with the inner cavity of the mask, the gas is continuously delivered from the proximal end of the mask to the mask cavity and discharged from the distal end, and at the same time, the expiratory gas is expelled from the distal end of the mask, so that the gas staying at the proximal end of the mask before inhalation is essentially the gas from the gas source or mixer, and does not contain the expiratory gas. The beneficial effect of the present invention is to ensure that the concentration of the gas delivered into the mask is exactly the same as the concentration of the gas that the patient breathes into the respiratory tract. By adjusting the concentration of the gas delivered by the gas source or the gas mixer, the gas entering the respiratory tract can be of any concentration, even 100% concentration (such as pure oxygen). Since no mask resistance exists during inhalation and exhalation and the gas is continuously delivered into the mask cavity with the catheter surrounding the mask with a plurality of small orifices to replace and clear the expiratory gas, the gas at the proximal air of the mask is always "fresh" gas from the gas mixer, thereby eliminating the retention of expiratory gas. Due to the large area of the large orifices or the huge orifice at the distal end of the mask, even if a small gap exists between the mask and the face, all the gas will still be discharged through the large orifices or the huge orifice at the distal end of the mask, avoiding facial pressure and discomfort caused by excessive tightening of the headband. Since the flow direction of the gas delivered to the mask is consistent with the flow direction of the expiratory gas, not only the discharge of the expiratory gas is not hindered, but also the emptying of the expiratory gas is accelerated to achieve smooth expiration without rebreathing, the concentration of the inhaled gas can be accurately adjusted, and a high-concentration gas inhalation can be achieved.

DETAILED DESCRIPTION

The present invention will be further described below in conjunction with the drawings and embodiments.

Figure 1:
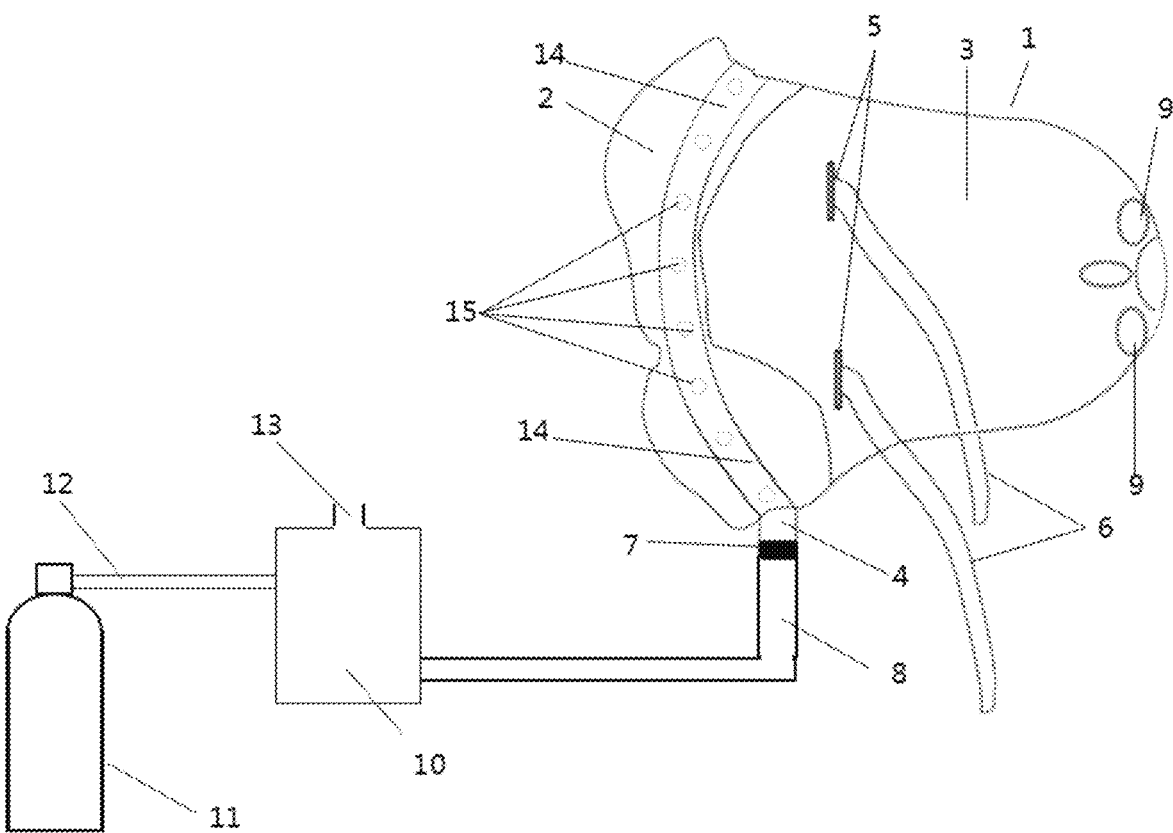
FIG. 1 is a schematic structural diagram of a first embodiment of a gas inhalation device with a constant concentration of gas entering the respiratory tract and without respiratory resistance according to the present invention.

FIG. 1 shows the appearance of a gas inhalation device. It includes a mask 1, a gas source 11, a gas mixer 10 and connecting pipes 8 and 12. The mask 1 includes a soft cushion 2 connected to the face and a mask body 3. The mask body 3 is capable of holding 50-1000 ml of gas. One or two headband fixing bayonets 5 are provided on both sides of the mask's outer layer and connected to a headband 6. An adapter tube 4 is provided at the cushion 2 at the proximal end of the mask. One end of the adapter tube 4 is connected to a catheter 14 surrounding the mask. A plurality of small orifices 15 communicating with the mask cavity are provided on the catheter. The gas delivery pipe 8 is connected to one end of the adapter tube 4 by a connector 7. The gas source 11 is a high-pressure gas, which is connected to the gas mixer 10 through the connecting pipe 12. The concentration of the gas entering the gas delivery pipe 8 can be accurately adjusted by controlling an air flow 13. When a patient wears the mask, the gas from the gas mixer 10 is delivered into the catheter 14 surrounding the mask through the gas delivery pipe 8 and the connector 7 to the adapter tube 4, and then enter the mask cavity through the plurality of small orifices 15 on the catheter from the cushion 2 at the proximal end of the mask. If the patient pauses breathing, the gas from the gas mixer 10 will flow from the proximal end of the mask to the distal end of the mask and exit from large orifices 9 at the distal end of the mask.

Figure 2:
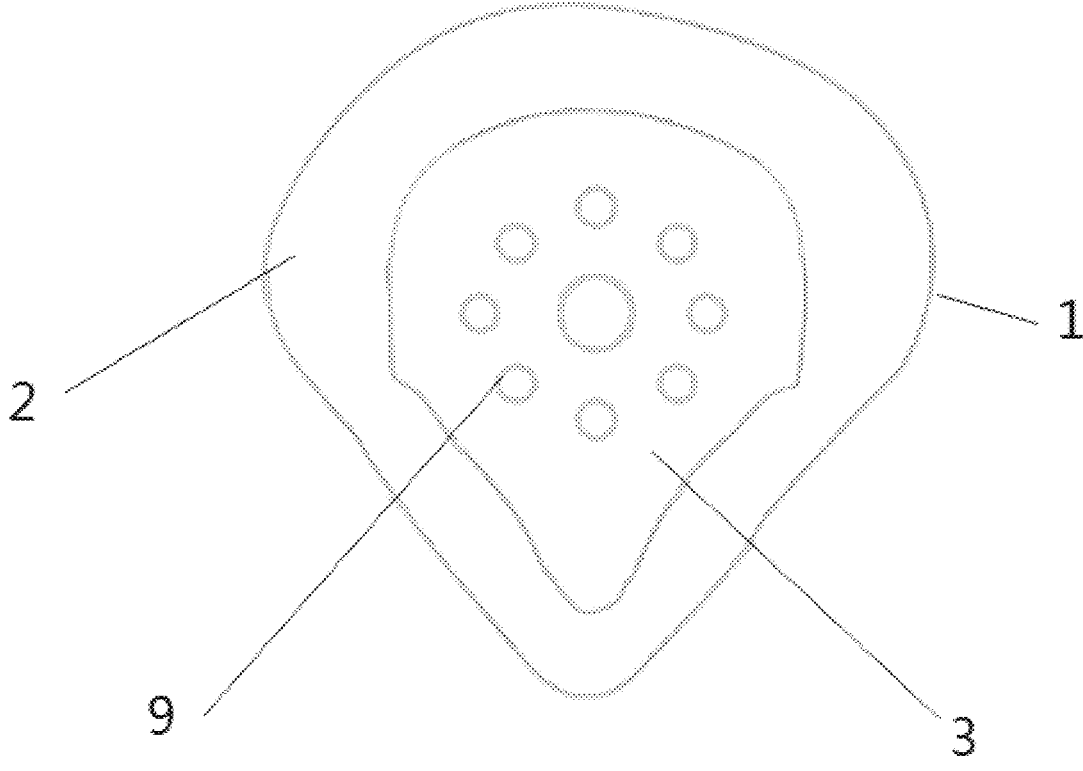
FIG. 2 is a front view of a mask of a gas inhalation device with a constant concentration of gas entering the respiratory tract and without respiratory resistance according to the present invention.

FIG. 2 is a front view of the mask 1, which includes the cushion 2 at the proximal end of the mask, the mask body 3 and a vent 9 at the distal end of the mask.

Figure 3:
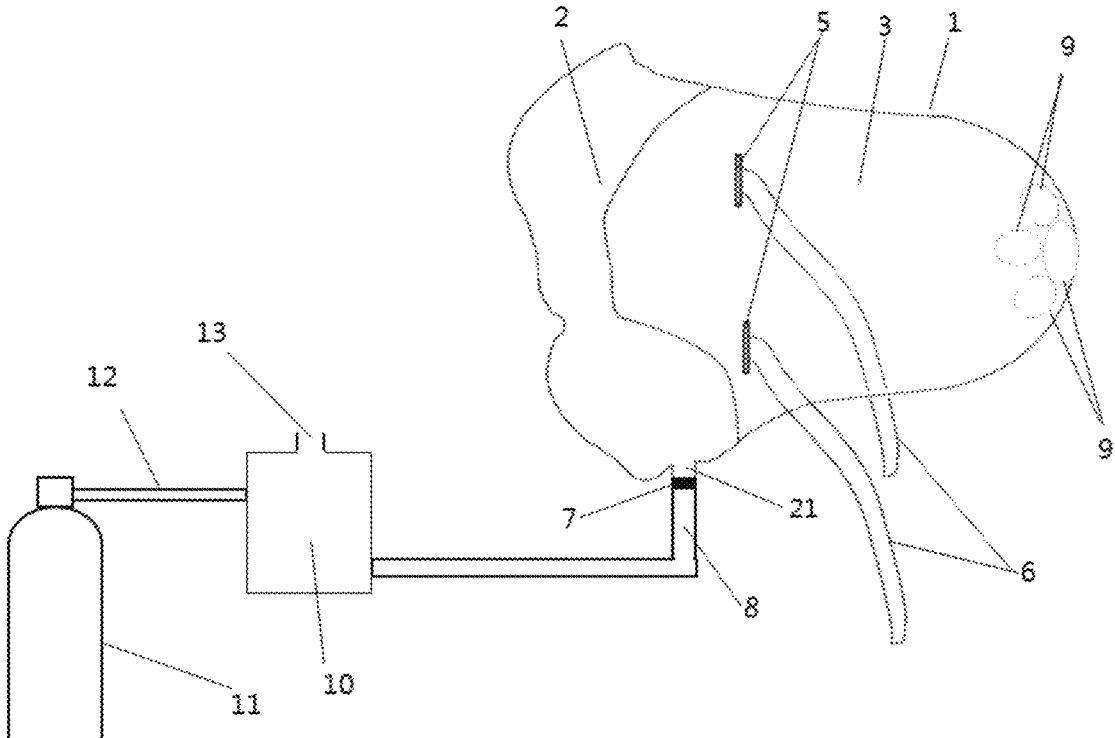
FIG. 3 is a schematic structural diagram of a second embodiment of a gas inhalation device with a constant concentration of gas entering the respiratory tract and without respiratory resistance according to the present invention.

FIG. 3 shows a simple way of connecting the gas delivery pipe to the mask, which includes the mask 1, the gas source 11, the gas mixer 10, and the connecting pipes 8 and 12. The mask 1 includes the soft cushion 2 connected to the face and the mask body 3. The mask body 3 is capable of holding 50-1000 ml of gas. One or two headband fixing bayonets 5 are provided on both sides of the mask's outer layer and connected to the headband 6. A straight-through tube 21 open to the mask cavity is provided at the cushion 2 at the proximal end of the mask. One end of the straight-through tube 21 is open to the mask cavity, and the other end is connected to the gas delivery pipe 8 via the connector 7. The gas source 11 is a high-pressure gas, which is connected to the gas mixer 10 through the connecting pipe 12. The concentration of the gas entering the gas delivery pipe 8 can be accurately adjusted by controlling an air flow 13. After the patient wears the mask, the gas from the gas mixer 10 is delivered into the mask cavity through the gas delivery pipe 8 and the connector 7 and then through the straight-through tube 21. If the patient pauses breathing, the gas from the gas mixer 10 will flow from the proximal end 2 of the mask to the distal end of the mask and exit from the large orifices 9 at the distal end of the mask.

Figure 4:
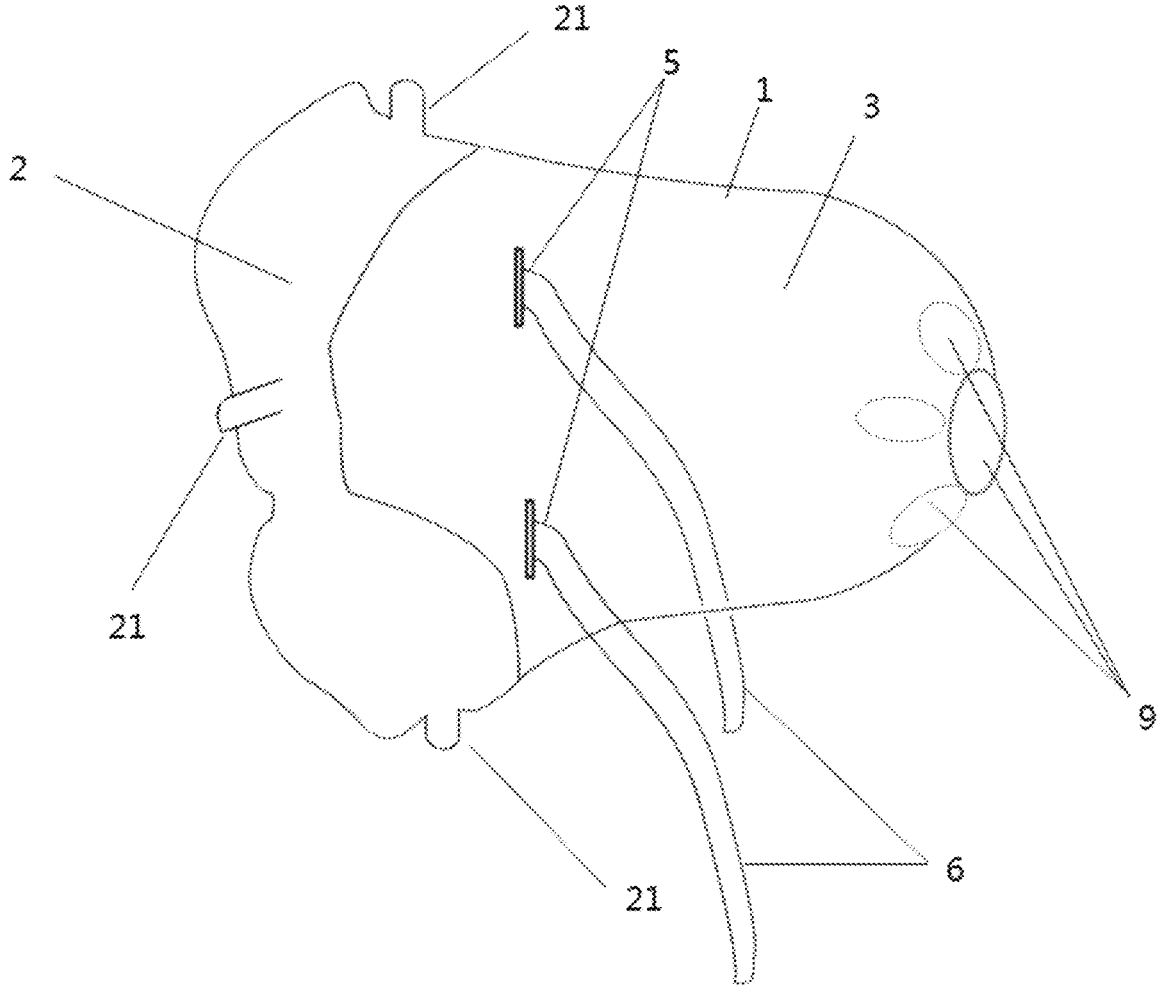
FIG. 4 is a schematic structural diagram of a mask of a third embodiment of a gas inhalation device with a constant concentration of gas entering the respiratory tract and without respiratory resistance according to the present invention.

FIG. 4 shows another way to connect the gas delivery pipe to the mask, which includes four straight-through pipes 21 open to the cavity of the mask at the cushion 2 at the proximal end of the mask. They are located on upper, lower, left and right sides of the proximal end of the mask for connecting the gas delivery pipe. One or two headband fixing bayonet are provided on both sides of the outer layer of the mask body 3 and connected to the headband 6 for fixing the mask when worn. A plurality of large orifices 9 are provided on the distal end of the mask for discharging the expiratory gas and the gas from the gas delivery pipe.

Figure 5:
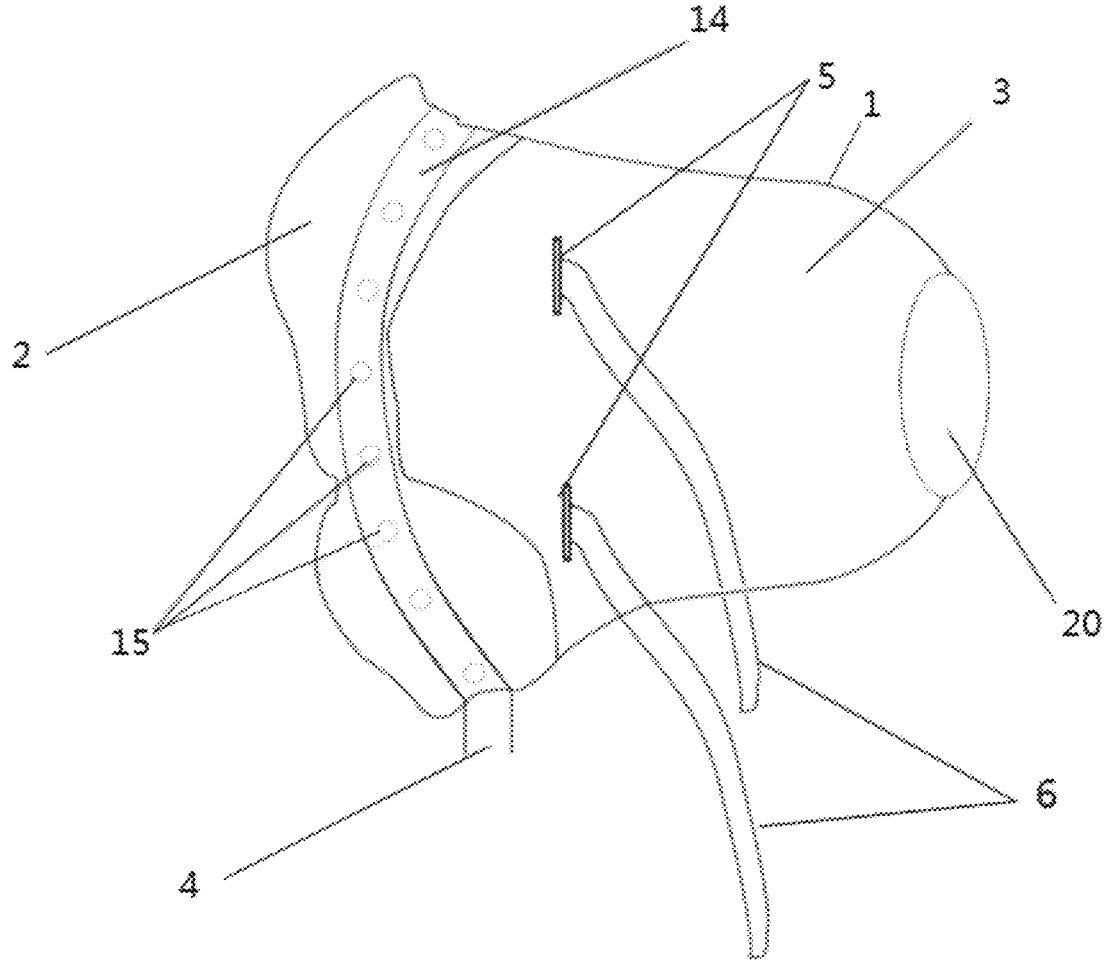
FIG. 5 is a schematic structural diagram of a fourth embodiment of a gas inhalation device with a constant concentration of gas entering the respiratory tract and without respiratory resistance according to the present invention.

FIG. 5 shows another type of mask vent. The mask 1 includes the soft cushion 2 connected to the face and the mask body 3. The mask body 3 is capable of holding 50-1000 ml of gas. One or two headband fixing bayonets 5 are provided on both sides of the mask's outer layer and connected to the headband 6. The adapter tube 4 is provided at the cushion 2 at the proximal end of the mask. One end of the adapter tube 4 is connected to the catheter 14 surrounding the mask. The plurality of small orifices 15 communicating with the mask cavity are provided on the catheter. The adapter tube 4 is used to connect the gas delivery pipe. One or two headband fixing bayonets 5 are provided on both sides of the outer layer of the mask body 3 and connected to the headband 6 for fixing the mask when worn. A huge orifice 20 with a diameter greater than 2 cm is provided at the distal end of the mask for discharging expiratory gas and discharging gas from the gas delivery pipe.

Figure 6:
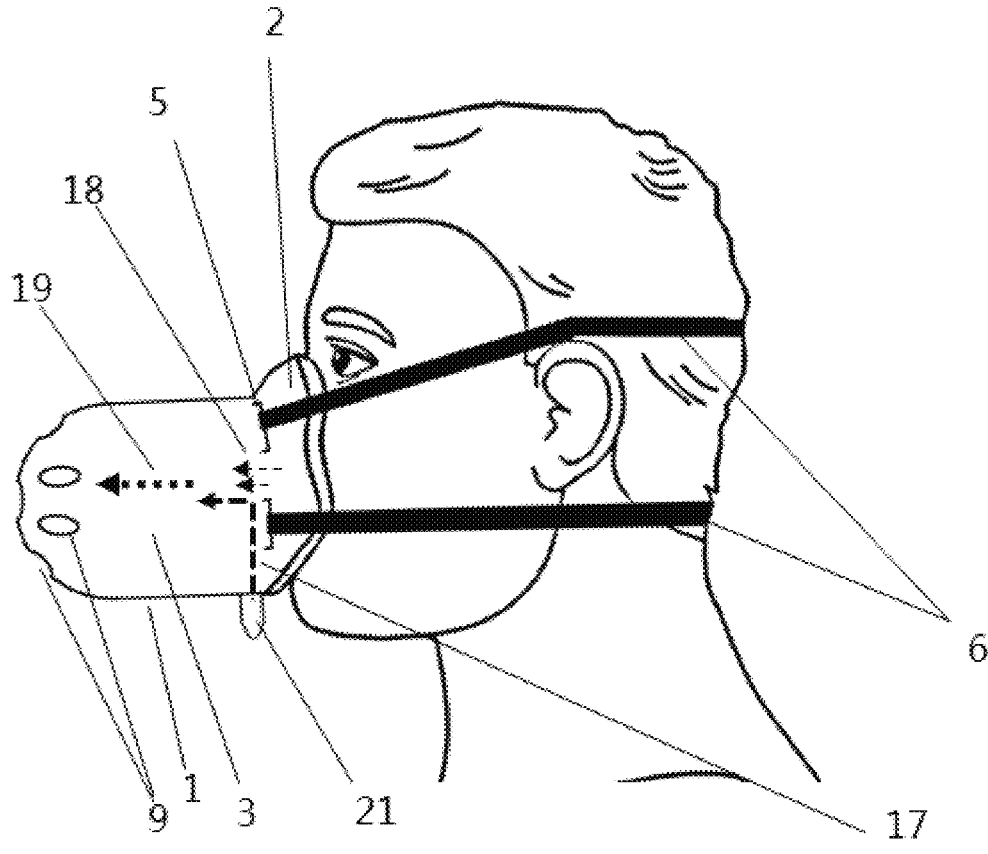
FIG. 6 is a schematic diagram of a first use state of a gas inhalation device with a constant concentration of gas entering the respiratory tract and without respiratory resistance according to the present invention.

FIG. 6 shows a working principle diagram A of the mask. The patient wears the mask 1 and fixes the mask 1 by connecting the headband 6 through the headband fixing bayonets 5. The proximal end of the mask 1 is provided with the cushion 2. The distal end of the mask 1 is provided with a plurality of large vents 9. When the gas delivery pipe is connected to the straight-through pipe 21, the gas in the gas delivery pipe will enter the mask cavity through the straight-through pipe 21. When the patient exhales, the gas flow will enter the mask cavity as shown by an arrow 17 and form a gas flow 19 together with the expiratory gas flow 18 to be discharged from the vent 9 at the distal end of the mask.

Figure 7:
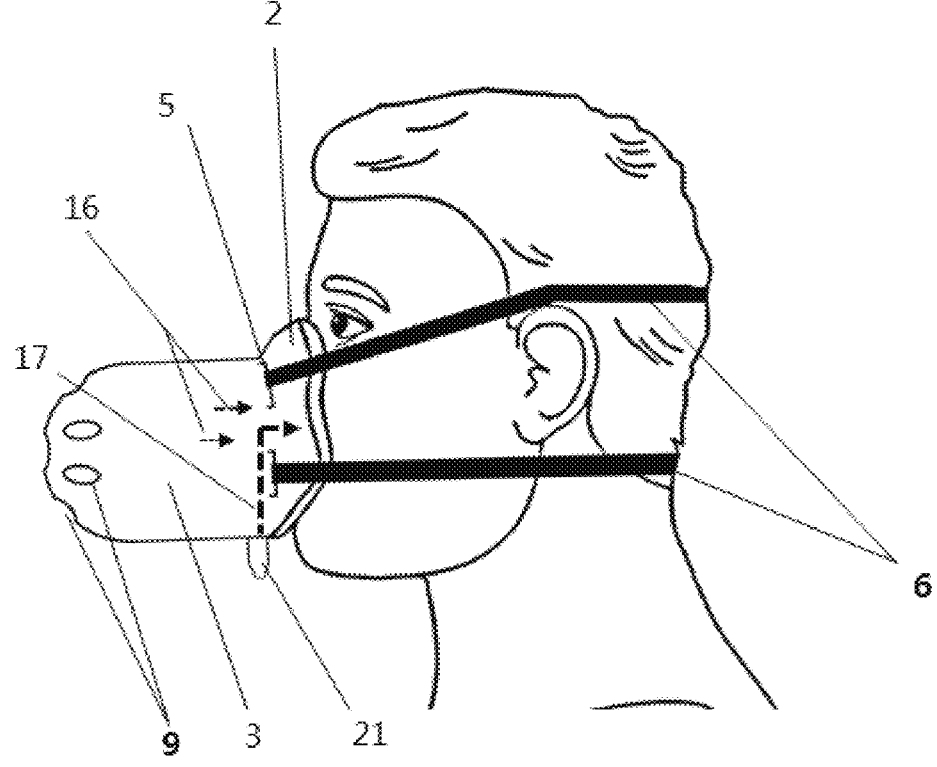
FIG. 7 is a schematic diagram of a second use state of a gas inhalation device with a constant concentration of gas entering the respiratory tract and without respiratory resistance according to the present invention.

FIG. 7 shows a working principle diagram B of the mask. The patient wears the mask 1 and fixes the mask 1 by connecting the headband 6 through the headband fixing bayonets 5. The proximal end of the mask 1 is provided with the cushion 2. The distal end of the mask 1 is provided with a plurality of large vents 9. When the gas delivery pipe is connected to the straight-through pipe 21, the gas in the gas delivery pipe will enter the mask cavity through the straight-through pipe 21. When the patient inhales, the gas flow will enter the mask cavity and enter the respiratory tract as shown by the arrow 17. If the inhaling flow rate is greater than the flow rate from the gas delivery pipe, part of gas 16 in the mask cavity will enter the respiratory tract. The gas 16 at the proximal end of the mask cavity is actually the gas from the gas delivery pipe after the exhalation stops and before the inhalation.

Figure 8:
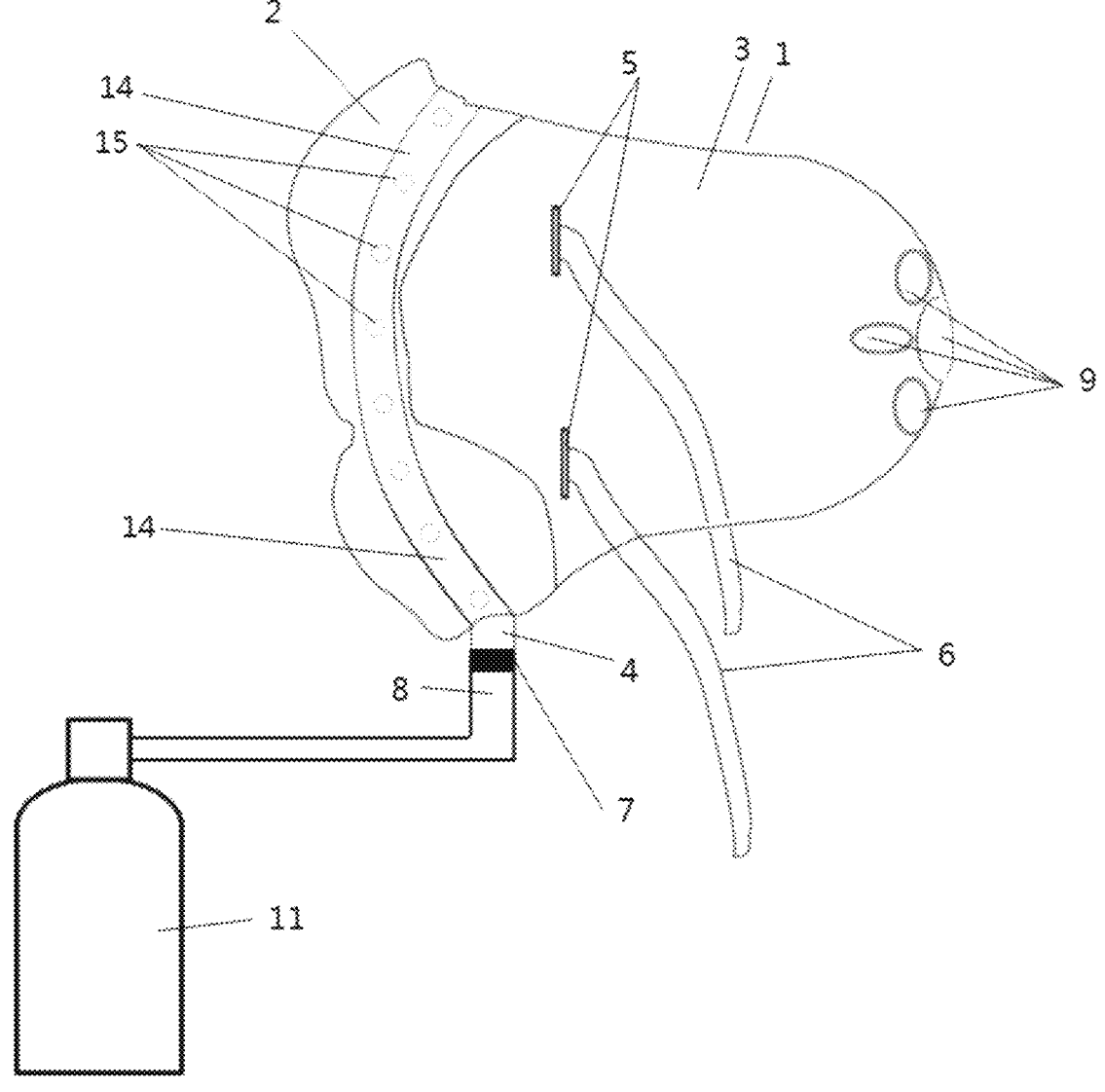
FIG. 8 is a schematic structural diagram of a gas inhalation device with a constant concentration of gas entering the respiratory tract and without respiratory resistance according to the present invention directly connected to a gas source.

FIG. 8 shows an appearance of the gas inhalation device in which the gas source is directly connected to the mask. The gas source 11 containing the required gas composition is connected to the catheter 14 surrounding the mask at the proximal end of the mask through the gas delivery pipe 8 via the connector 7 and the adapter 4, and delivers gas evenly into the mask cavity through the small orifices 15 on the catheter. After the patient fixes the mask 1 on the face with the headband fixing bayonets 5 and the headband 6, if the patient pauses breathing, the gas from the gas delivery pipe 8 will enter from the proximal end of the mask 1 and exit from the large orifices 9 at the distal end of the mask.

The principle of use of the gas inhalation device will be further described hereinafter with reference to FIGS. 1-8:

The patient wears the mask 1 so that the cushion 2 at the proximal end of the mask 1 fits the face, and fixes the mask 1 by the headband 6 and the fixing bayonets 5. Through the adapter tube 4 at the proximal end of the mask, the mask 1 is connected to the gas delivery pipe 8 by means of the connector 7. The gas concentration in the gas delivery pipe 8 is adjusted by the gas mixer 10. The gas mixer adjusts the flow rate and concentration of the gas delivered into the mask cavity by adjusting the high-pressure gas source 11 and the air flow 13 and the ratio thereof. For example, to treat central sleep apnea by inhaling low-concentration $CO_2$, assuming that the flow rate delivered to the gas delivery pipe 8 by the gas mixer is 60 liters/min, the $CO_2$ concentration is 1%, and the 1% $CO_2$ in the gas delivery pipe 8 passes through the connector 7 to the adapter tube 4 and is then delivered to the catheter 14 and then uniformly delivered from the proximal end of the mask to the mask cavity through the small orifices 15 on the catheter and communicated with the mask cavity for the patient to inhale or flowing to the distal end of the mask and exiting from the large orifices 9 at the distal end. When the patient pauses breathing, the gas entering the mask cavity through the small orifices 15 will all exit from the large orifices 9 at the distal end of the mask. Due to the existence of the plurality of large orifices 9 at the distal end of the mask, on the one hand, all the gas flow from the small orifices 15 is discharged from the large orifices 9; and on the other hand, due to the large area of the large orifices 9, it can ensure that the pressure in the mask is always zero. According to fluid mechanics, even if a tiny gap exists between the mask and the face, the gas flow will not enter and exit from the tiny gap. As shown in FIG. 6, when the patient exhales, a flow direction 17 of the gas from the gas delivery pipe 8 in the mask is consistent with a flow direction 18 of the patient's expiratory gas, forming a gas flow 19. The gas flow from the gas delivery pipe will not hinder the discharge of the expiratory gas, but accelerates the discharge of the expiratory gas from the large orifices 9 at the distal end of the mask, reducing the retention of expiratory gas and eliminating the influence of expiratory gas on the concentration of inhaled gas. As shown in FIG. 7, when the patient inhales, the gas 17 from the gas delivery pipe will flow to the respiratory tract due to a negative pressure generated by the breathing power. If the gas flow rate from the gas delivery pipe cannot meet the needs of the patient, the gas 16 in the mask cavity will also be inhaled into the respiratory tract. In the initial stage of inhalation, the gas in the mask cavity is actually the remaining gas from the gas delivery pipe in the mask cavity after the expiratory gas is expelled from the large orifices 9, which has the same gas composition as the gas delivery pipe and almost contains no expiratory gas. Assuming that the patient's tidal volume is 1200 ml, the breathing rate is 15 beats/min, the inhalation time is 1.5 seconds, the expiration time is 1.5 seconds, and the breath holding time is 1 second, then 1000 ml of gas delivered in the mask for one second stays in the mask cavity. Even if the patient's inhaling flow rate is greater than the gas delivery rate, the composition of the gas from the mask cavity is exactly the same as that of the gas from the gas delivery pipe, that is, 1% $CO_2$ gas. To further illustrate the principle of the gas inhalation device, assuming that the mask volume is 1000 ml, the flow rate from the gas mixer is 30 liters/min, the patient's breathing rate is 15 breaths/min, the inhalation time and expiration time are also 1.5 seconds, and the breath holding time is also 1 second, then the proximal end of the mask cavity has 500 ml of gas delivered with a delivery time of one second. In this case, even if the patient's inhaling flow rate is greater than the gas delivery rate, the 500 ml of gas from the proximal end of the mask cavity has exactly the same composition as that of the gas delivery pipe, namely 1% $CO_2$ gas. It is impossible to inhale the gas containing expiratory gas composition that stay at the distal end of the mask until the tidal volume exceeds 1250 ml. Due to the large vents at the distal end of the mask and the fresh gas output by the gas mixer being continuously delivered to the mask cavity, not only the patient can breathe smoothly, without breathing difficulty, but also accurate inspiratory gas concentration can be maintained.

As another example, if the mask volume is chosen to be 500 ml and 100% oxygen is to be inhaled, as shown in FIG. 1, all the gas sources entering the gas mixer come from 100% oxygen through the gas mixer and by shutting off the air flow 13. If the patient's tidal volume is 600 ml, the patient's breathing rate is 20 beats/min, the inhalation time is 1 second, the exhalation time is 1.5 seconds, and the interval between inhalation and exhalation is 0.5 seconds, the flow rate of the gas delivery pipe is 30 liters/min by adjusting the gas mixer 10. That is, the gas delivery volume per second from the gas delivery pipe is 500 ml. As the gas from the gas delivery pipe continues to infuse the mask to expel the expiratory gas, at the beginning of inhalation, still 250 ml of gas from the gas delivery pipe and almost without expiratory gas stays at the proximal end of the mask, which is sufficient to compensate for the dynamic flow rate from the gas delivery pipe not enough to satisfy the patient's gas volume.

Figure 9:
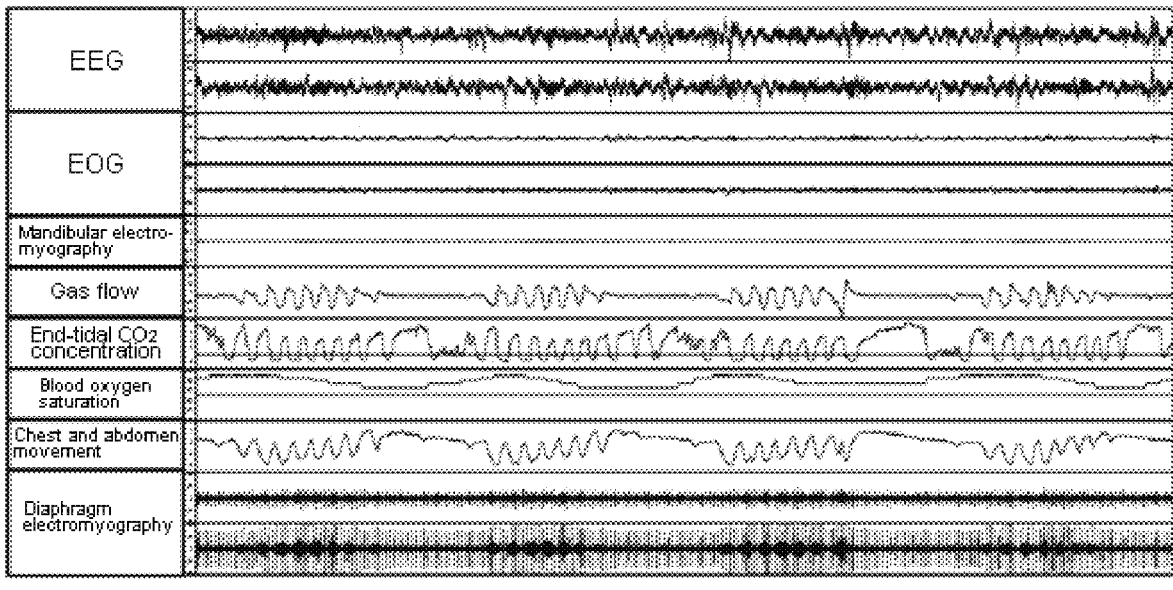
FIG. 9 is a polysomnogram before treatment.
Figure 10:
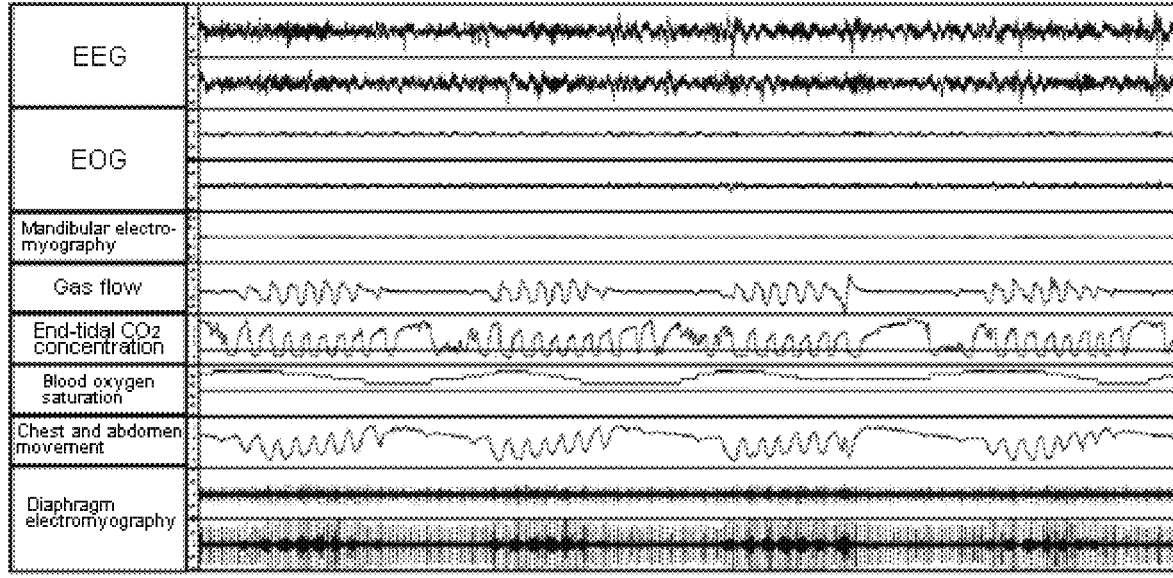
FIG. 10 is a polysomnogram after treatment.

A treatment case of a patient with severe central sleep apnea due to left heart failure is described hereinafter. The patient's tidal volume is 500 ml, the breathing rate is 20 beats/min, and the inhaled $CO_2$ concentration required to eliminate the patient's central sleep apnea is 1%. In order to ensure a constant concentration of inhaled $CO_2$, the gas delivery rate output by the gas mixer 10 is chosen to be 40 liters/min. For the purpose of treatment, the gas source 11 containing 100% $CO_2$ is used and connected to the gas mixer 10 through the connecting pipe 12, and the flow rate output by the gas mixer 10 to the gas delivery pipe 8 is 40 liters/min by adjusting the gas mixer 10 to control the gas from the air flow 13. After the patient wears the mask 1 and fixes the mask 1 with the headband 6, the gas delivery pipe 8 injects 1% $CO_2$ gas from the gas mixer 10 into the mask cavity at a uniform flow rate of 40 liters/min through the connector 7 and then the adapter tube 4 and the catheter 14 and then through the small orifices 15 on the catheter 14 for inhalation by the patient or flowing to the distal end of the mask 1 and exiting from the large orifices 9 at the distal end. When the patient pauses breathing, the gas entering the mask cavity through the small orifices 15 will all exit from the large orifices 9 at the distal end of the mask. Due to the existence of the plurality of large orifices 9 at the distal end of the mask, on the one hand, all the gas flow from the small orifices 15 is discharged from the large orifices 9; and on the other hand, due to the large area of the large orifices 9, it can ensure that the pressure in the mask is always zero. Since the gas from the gas mixer continues to be continuously delivered to the mask cavity including the expiratory phase, accelerating the discharge of the expiratory gas and avoiding the retention of the expiratory gas. Through the gas inhalation device, the patient's central sleep apnea event disappears, and the sleep quality is improved. FIG. 9 and FIG. 10 are the polysomnograms before and after treatment, respectively. Before treatment (FIG. 9), intermittent apnea events occurred in the airflow channel, which was manifested by the disappearance of the airflow signal gap. After treatment with the gas inhalation device (FIG. 10), the apnea event disappeared and the airflow signal became regular. The results before and after the treatment further illustrate the value of the gas inhalation device.

In addition to the above implementation examples, the following variations also belong to the scope of the present invention:

1. In addition to using a gas mixer, gas with a constant concentration and flow rate can also be pre-prepared and stored in a high-pressure gas cylinder.

2. The catheter at the proximal end of the mask for delivering gas to the mask cavity is provided with a plurality of small orifices. The catheter can be placed above and below the mask, on the left and right sides, or around the outside of the mask, and may also be inlaid on the inner wall of the mask.

The above-mentioned specific implementations are preferred embodiments of the present invention and do not limit the present invention. Any other changes or other equivalent replacement methods that do not deviate from the technical solutions of the present invention are included in the protection scope of the present invention.

What is claimed is:

1. A gas inhalation device with a substantially constant concentration of gas entering a respiratory tract and substantially without respiratory resistance, comprising:

an open mask and a gas source, wherein the mask is a container that is capable of holding 250-1000 ml of gas, a proximal end of the mask is a soft cushion for fitting a face of a user and surrounded by a gas delivery tube, the gas delivery tube is provided with a plurality of gas delivery orifices configured to communicate with an inner cavity of the mask, one end of the gas delivery tube is connected to one end of an adapter tube, the other end of the adapter tube is connected to a gas delivery pipe, the gas delivery pipe is configured to connect the adapter tube and the gas source;

a terminal end of the mask is provided with a vent comprising one or more discharge orifices; when the user wears the mask and the mask is communicated with the gas source, the gas from the gas source is configured to be continuously delivered into the cavity at the proximal end of the mask at a constant concentration and flow rate through the gas delivery pipe and the gas delivery tube, and configured to be discharged from the one or more discharge orifices at the terminal end of the mask and configured to expel expiratory gas of the user from the one or more discharge orifices at the terminal end of the mask;

wherein a total area of the one or more discharge orifices is configured to allow gas to flow in and out substantially without airflow resistance;

wherein the total area of the one or more discharge orifices is configured such that an internal pressure of the cavity is substantially equal to an ambient pressure outside the mask during continuous injection of gas into the cavity;

wherein the mask extends forward from the proximal end to terminate at a terminal end of the mask and forms an intermediate portion between the proximal end and the terminal end, and the one or more discharge orifices at the terminal end of the mask.

2. The gas inhalation device according to claim 1, wherein the mask is an open mask that is capable of holding within a range of 250 ml and 1000 ml of gas.

3. The gas inhalation device according to claim 1, wherein the mask is configured to be attached to the face to avoid leakage without applying pressure to seal on the face.

4. The gas inhalation device according to claim 1, wherein the gas from the gas source enters the cavity from the proximal end of the mask for the user to inhale or to be discharged from the one or more discharge orifices at the terminal end.

5. The gas inhalation device according to claim 1, wherein the gas source comprises a gas mixer, a gas cylinder or a hospital central gas supply system.

6. The gas inhalation device according to claim 1, wherein if the gas flow from a gas mixer is unable to meet inhalation needs of the user, the gas from the gas source staying at the proximal end of the mask before inhaling is used as a supplement to keep the concentration of the gas entering the respiratory tract substantially unchanged.

7. The gas inhalation device according to claim 1, wherein a headband interface is provided on each of two outer sides of the mask for connecting a headband configured to fix the mask to the face.

8. The gas inhalation device according to claim 1, wherein the proximal end of the mask is provided with one or more inlets communicating with the cavity to receive the gas from the gas source.

9. The gas inhalation device according to claim 8, wherein the mask is configured to be attached to the face without applying pressure to seal.

10. The gas inhalation device according to claim 1, wherein the one or more discharge orifices consist of one single discharge orifice located substantially in the center of the terminal end of the mask.

11. The gas inhalation device according to claim 10, wherein the one single discharge orifice has a diameter greater than 2 cm.

12. The gas inhalation device according to claim 1, wherein the gas delivered into the cavity can be any one of oxygen, $CO_2$, hydrogen, helium, or any combination thereof, and the concentration of the gas delivered into the cavity is substantially equal to that of the gas entering the respiratory tract.

13. The gas inhalation according to claim 12, wherein the concentration of the gas delivered into the cavity is selectable.

14. The gas inhalation device according to claim 13, wherein the gas delivered into the cavity comprises oxygen at a concentration from 21% to 100%.

15. The gas inhalation device according to claim 13, wherein the gas delivered into the cavity comprises $CO_2$ at a concentration from 0% to 10%.

16. A gas inhalation device with a substantially constant concentration of gas entering a respiratory tract and substantially without respiratory resistance, comprising:

an open mask and a gas source, wherein the mask is a container that is capable of holding 500-1000 ml of gas, a proximal end of the mask is a soft cushion for fitting a face of a user and surrounded by a gas delivery tube, the gas delivery tube is provided with a plurality of gas delivery orifices configured to communicate with an inner cavity of the mask, one end of the gas delivery tube is connected to one end of an adapter tube, the other end of the adapter tube is connected to a gas delivery pipe, the gas delivery pipe is configured to connect the adapter tube and the gas source;

a terminal end of the mask is provided with a vent comprising one or more discharge orifices; when the user wears the mask and the mask is communicated with the gas source, the gas from the gas source is configured to be continuously delivered into the cavity at the proximal end of the mask at a constant concentration and flow rate through the gas delivery pipe and the gas delivery tube, and configured to be discharged from the one or more discharge orifices at the terminal end of the mask and configured to expel expiratory gas of the user from the one or more discharge orifices at the terminal end of the mask;

wherein a total area of the one or more discharge orifices is configured to allow gas to flow in and out substantially without airflow resistance;

wherein the total area of the one or more discharge orifices is configured such that an internal pressure of the cavity is substantially equal to an ambient pressure outside the mask during continuous injection of gas into the cavity;

wherein the mask extends forward from the proximal end to terminate at a terminal end of the mask and forms an intermediate portion between the proximal end and the terminal end, and the one or more discharge orifices at the terminal end of the mask.

* * * * *